(12) United States Patent
Marcus

(10) Patent No.: US 10,980,585 B2
(45) Date of Patent: Apr. 20, 2021

(54) INTERMAXILLARY FIXATION DEVICE AND METHOD OF USING SAME

(71) Applicant: Jeffrey R. Marcus, Chapel Hill, NC (US)

(72) Inventor: Jeffrey R. Marcus, Chapel Hill, NC (US)

( * ) Notice: Subject to any disclaimer, the term of this patent is extended or adjusted under 35 U.S.C. 154(b) by 274 days.

(21) Appl. No.: 15/775,256

(22) PCT Filed: Nov. 11, 2016

(86) PCT No.: PCT/US2016/061525
§ 371 (c)(1),
(2) Date: May 10, 2018

(87) PCT Pub. No.: WO2017/083644
PCT Pub. Date: May 18, 2017

(65) Prior Publication Data
US 2018/0353230 A1     Dec. 13, 2018

Related U.S. Application Data

(60) Provisional application No. 62/253,802, filed on Nov. 11, 2015, provisional application No. 62/319,691, filed on Apr. 7, 2016.

(51) Int. Cl.
| | | |
|---|---|---|
| *A61C 8/00* | (2006.01) | |
| *A61C 7/36* | (2006.01) | |
| *A61B 17/80* | (2006.01) | |
| *A61B 17/86* | (2006.01) | |
| *A61C 7/20* | (2006.01) | |

(52) U.S. Cl.
CPC ............ *A61B 17/8071* (2013.01); *A61C 7/20* (2013.01); *A61C 7/36* (2013.01); *A61C 8/0096* (2013.01)

(58) Field of Classification Search
CPC ... A61B 17/842; A61B 17/86; A61B 17/8071; A61C 8/0096; A61C 8/00; A61C 7/36; A61C 7/20; A61C 7/00
USPC ......... 606/70–71, 280–299; 433/2, 18–19, 7, 433/173–174
See application file for complete search history.

(56) References Cited

U.S. PATENT DOCUMENTS

| | | | | |
|---|---|---|---|---|
| 4,230,104 A | * | 10/1980 | Richter | ............... A61F 5/05891 433/18 |
| 5,087,202 A | * | 2/1992 | Krenkel | ................. A61C 5/007 433/19 |
| 5,681,313 A | * | 10/1997 | Diez | .................. A61B 17/8004 606/282 |

(Continued)

OTHER PUBLICATIONS

International Search Report and Written Opinion on International Patent Application No. PCT/US2016/061525 dated Feb. 16, 2017. 12 pages.

*Primary Examiner* — Jessica Weiss
(74) *Attorney, Agent, or Firm* — Foley & Lardner LLP

(57) ABSTRACT

A method for fixating or stabilizing a subject's mandible and maxilla includes providing multiple bone fasteners, providing two arch bars, attaching a first grouping of the bone fasteners to the subject's mandible, then securing the first arch bar to the first grouping of bone fasteners, attaching a second grouping of the bone fasteners to the subject's maxilla, then securing the second arch bar to the second grouping of bone fasteners, and then fastening the first arch bar to the second arch bar.

8 Claims, 10 Drawing Sheets

(56) References Cited

U.S. PATENT DOCUMENTS

| | | |
|---|---|---|
| 8,992,582 B1 * | 3/2015 | Knoepfle ............ A61B 17/8028 606/281 |
| 2002/0127510 A1 | 9/2002 | Kyung et al. |
| 2007/0122764 A1 * | 5/2007 | Balfour ................ A61C 8/0089 433/19 |
| 2008/0050691 A1 * | 2/2008 | Baughman ........... A61C 8/0096 433/18 |
| 2009/0170050 A1 * | 7/2009 | Marcus .............. A61B 17/6433 433/18 |
| 2013/0065191 A1 | 3/2013 | Carrillo Fuentevilla et al. |
| 2014/0134564 A1 | 5/2014 | Baker |
| 2015/0059770 A1 * | 3/2015 | Shah ...................... A61B 17/82 128/861 |
| 2015/0150611 A1 * | 6/2015 | Marcus .................. A61C 5/007 606/328 |
| 2016/0008042 A1 * | 1/2016 | Woodburn, Sr. ... A61B 17/8071 606/328 |
| 2016/0106486 A1 * | 4/2016 | Marcus ................ A61C 8/0096 606/308 |
| 2018/0221069 A1 * | 8/2018 | Kohler ............... A61B 17/8071 606/280 |

\* cited by examiner

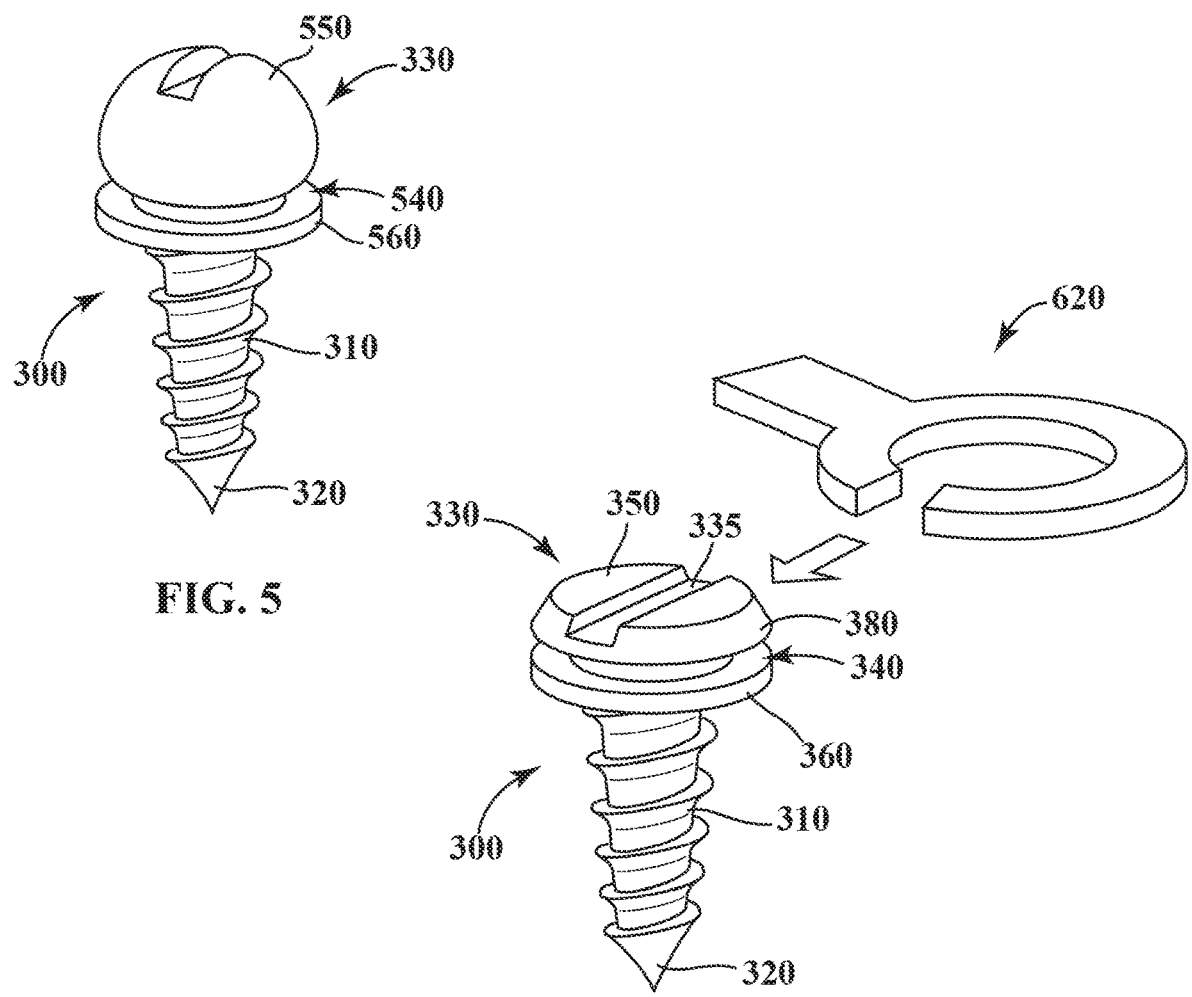
FIG. 5
FIG. 6
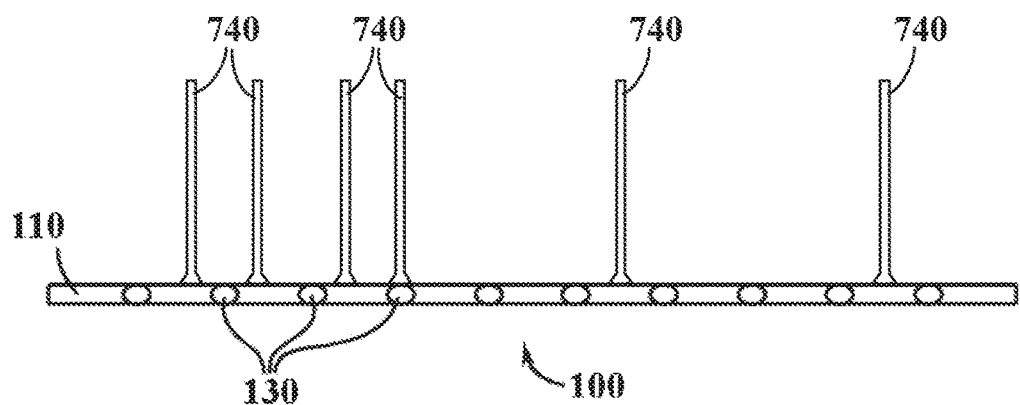
FIG. 7

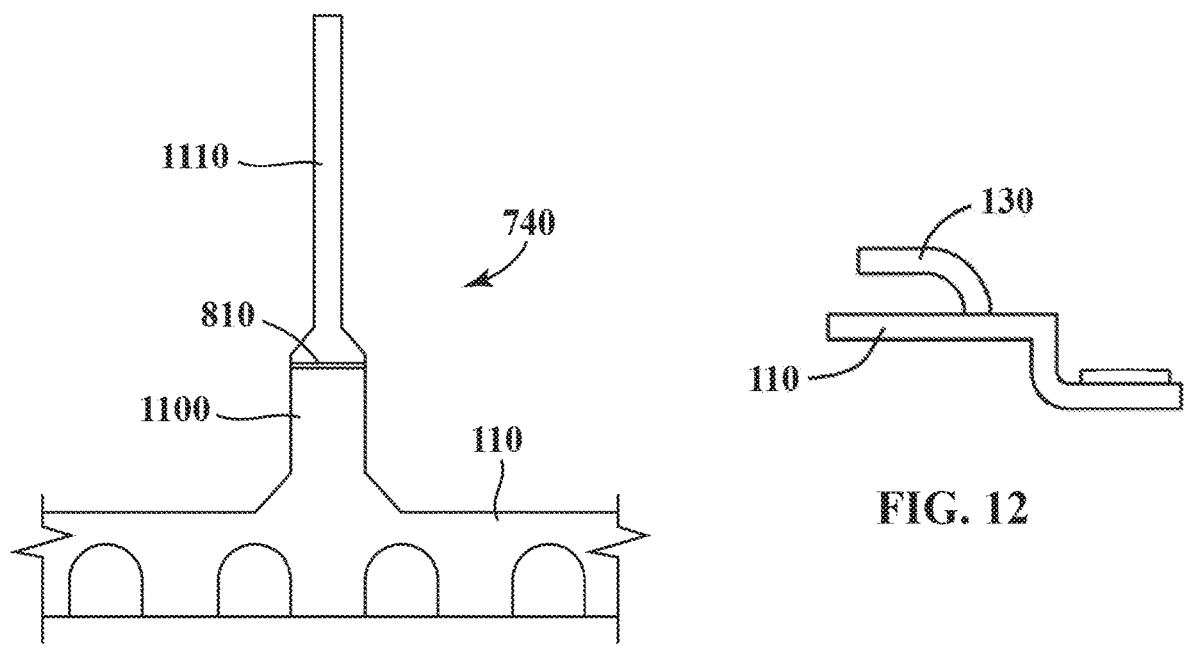
FIG. 11
FIG. 12
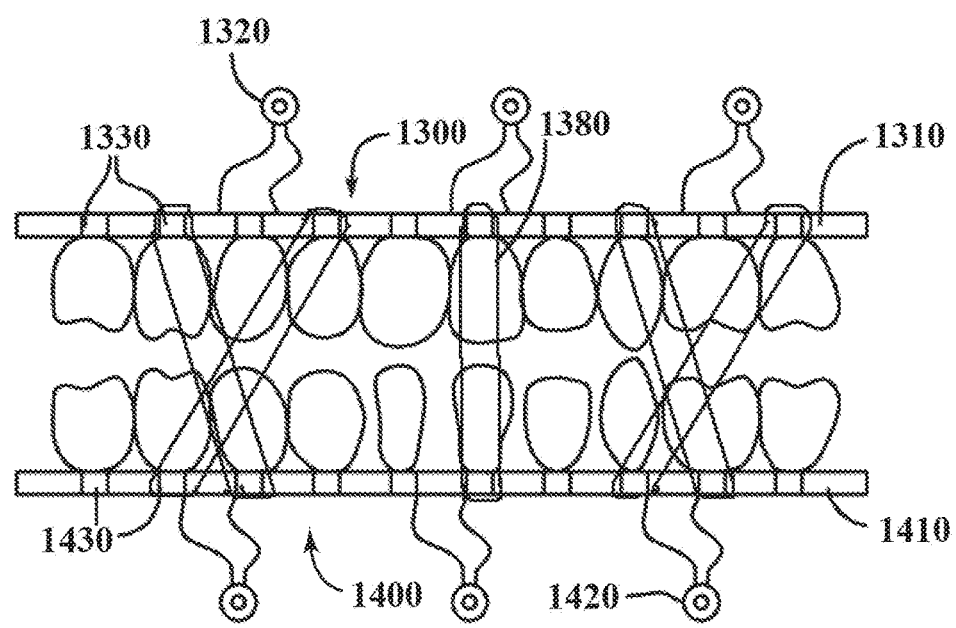
FIG. 13

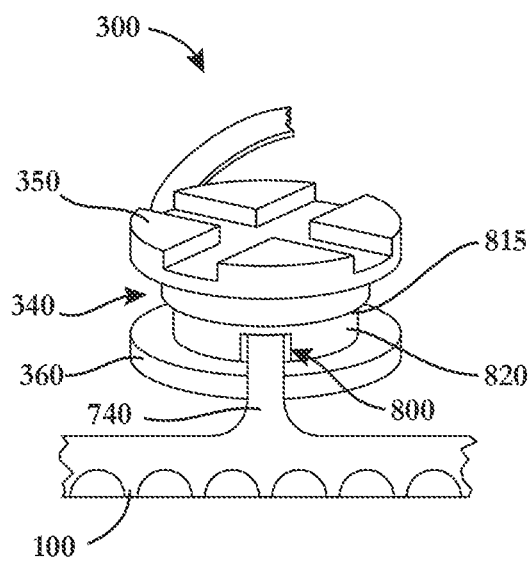
FIG. 24
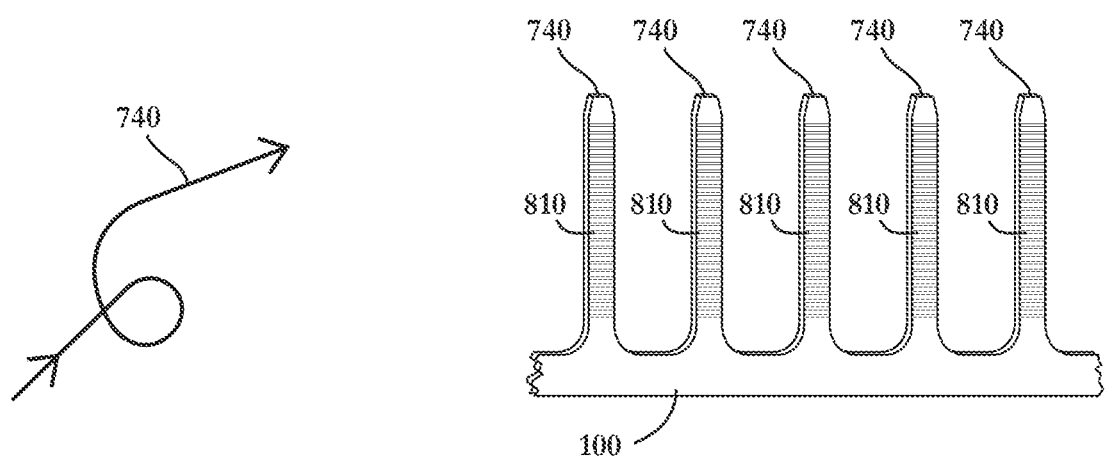
FIG. 25
FIG. 26

INTERMAXILLARY FIXATION DEVICE AND METHOD OF USING SAME

CROSS-REFERENCE TO RELATED APPLICATIONS

This application is a U.S. National Stage Application under 35 U.S.C. § 371 of PCT/US2016/061525, filed Nov. 11, 2016, which claims the benefit of and priority to U.S. Provisional Application No. 62/319,691, filed on Apr. 7, 2016, and U.S. Provisional Application No. 62/253,802, filed on Nov. 11, 2015. The contents of each application are incorporated herein by reference in their entirety.

FIELD

The invention is generally related to maxillofacial/dental devices. More specifically, the invention is related to devices for the maxillary and/or mandibular fixation or stabilization.

The fixation or stabilization of the upper and lower dental occlusal arches to one another is known as intermaxillary fixation (IMF), also known as maxillo-mandibular fixation (MMF). IMF has historically been a necessity in the treatment of all reconstructive jaw procedures.

BACKGROUND

The fixation or stabilization of the upper and lower dental occlusal arches to one another is known as intermaxillary fixation (IMF), also known as maxillo-mandibular fixation (MMF). IMF has historically been a necessity in the treatment of all reconstructive jaw procedures.

The earliest methods for providing IMF consisted of wiring techniques, in which metallic wires were placed around one or more (adjacent) teeth at their base(s) and were then twisted down to the teeth in a secure manner. When a wire is passed around a tooth (or teeth) at the base in such a way, it may be termed a circumdental wire ligature (CW). Multiple CW's can be placed along the span of the dental arch in a series, or the wire may also be fashioned such that a single continuous strand incorporates multiple teeth along the arch securely. In whatever manner this is accomplished, both upper and lower arches are so treated, and subsequently the jaws are then secured to one another with wire loops or elastics incorporating single or multiple CW or the opposing jaws, thus accomplishing IMF.

Arch bars (or arch wires) are known to those of skill in the art. Arch bars involve the use of a linear metal bar or wire that may be applied and secured to the dental arch form. Arch bars typically have a plurality of hooks/tabs facing in a single direction. The arch bars and their corresponding hooks are placed in opposing directions for the upper and lower jaws so that wire loops or elastics could securely affix the jaws together. Multiple types of arch bar have been proposed. Arch bars have the advantage of stability. The relatively rigid bar spanning along the dental arch provides stability along the upper border of either jaw even when a fracture is present between teeth. A plurality of hooks allows placement of elastics or wire loops between the jaws at varying angles to potentially affect varying, advantageous tension vectors. Two common methods of securing arch bars are (1) via circumdental wire ligatures, placed around the teeth in routine fashion but incorporating the arch bar; and (2) via orthodontic adhesives of a variety of types.

However, both of these methods suffer drawbacks. For example, the most common means to secure arch bars is via multiple circumdental wire ligatures. This is a time-consuming process, associated with significant discomfort and potential for dental injury. The wire ligatures themselves are uncomfortable and often must be adjusted/tightened by the treating physician. Removal of arch bars applied using CW's, is equally uncomfortable; there is further associated potential for dental injury; in some, removal requires operative anesthesia.

While orthodontic adhesives are known, they too have disadvantages, in large part due to the conditions under which IMF is performed. For example, IMF is often performed by a surgical specialist, who is unfamiliar with the techniques and procedures used by orthodontists and dentists in the area of dental adhesives. The procedures are also, many times, conducted in a trauma setting where damage and blood loss limit the ability to work with such adhesives—which require a relatively clean, dry field for efficacy.

Adhesive techniques and circumdental wiring techniques both require adequate dentition. Both techniques may be severely limited or even precluded in conditions for dental injury, loss, or preexisting poor dental health.

Another method of IMF is also known by utilizing individual screws, placed in the bone between tooth roots, with a portion of the screw projecting external to the gingival or mucosa. Two or more IMF screws are typically placed into each of the upper and lower jaws. A wire loop is then either wrapped around the exposed portion of two opposing screws, or through a hole that is drilled through each of the two opposing screw heads, to provide IMF.

The advantages of IMF screw fixation are speed of placement and comfort. The screws rarely require adjustment, are well-tolerated, and are easily removed. However, IMF screws do not provide stability along the dental arch as does an arch bar. Ideally, IMF is used not only for immobilization, but also for accurate restoration of occlusion. For fractures occurring between teeth, IMF screws do not provide upper border stabilization nor flexible technical application methods to optimize occlusion. Finally, it is difficult (if not impossible) to apply elastics between IMF screws. Elastic IMF is safer than wiring the jaws together, and is often preferred for specific fracture types in which the surgeon would prefer the patient to have guided mobility of the jaws rather than relative immobilization.

Most of the technologies proposed for IMF technologies to date have been developed by orthodontists and oral surgeons. These dental specialists have been understandably inclined to consider only methods which involve fixation to teeth, a concept that has been historically accepted and perpetuated since the early 1900's. The most significant developments in reconstructive jaw surgery in the modern era have focused largely on methods for internal fixation (plating), rather than IMF. However, internal fixation is not a replacement for IMF, nor does is preclude the need for IMF in most cases, which is still a mandatory procedure for reconstruction of the dental arches.

Despite developments in dental arch fixation technology, and advanced developments in other dental areas, the need to improve how to anchor arch bars to bone remains.

BRIEF DESCRIPTION OF THE DRAWINGS

FIG. 5 is a perspective view of an arch bar fastener, according to another embodiment.

FIG. 6 is a perspective view of the arch bar fastener of FIG. 3 and an attachment loop of an arch bar, according to another embodiment.

FIG. 7 is frontal view of an arch bar prior to bending to approximate the shape of a mandible or a maxilla, according to another embodiment.

FIG. 11 is detail frontal view of an elongated stem of an arch bar, according to one embodiment.

FIG. 12 is a side view of a hook, with cross-section of the bar, according to one embodiment.

FIG. 13 is a panoramic view of a full dental arch having a first and second arch bar in place across the dentition, according to one embodiment.

FIG. 24 is a perspective view of the screw of FIG. 23 and an arch bar.

FIG. 25 is a schematic view of a stem insertion and wrapping path, according to one embodiment.

FIG. 26 is a side view of an arch bar, according to one embodiment.

DETAILED DESCRIPTION

Arch bars are described for providing stabilization and/or fixation between the mandible and maxilla using device(s) affixed to bone (native or graft) or prosthedontic appliances for use in applications including, but not limited to, treatment of fracture, restoration and fixation of dental occlusion, and maxillary and/or mandibular reconstruction with or without bone grafts. The arch bars may be affixed to bone via bone fasteners (e.g., screws) or the use of adhesives), thus precluding the need for CW.

According to an exemplary embodiment, the bone fasteners are attached to the maxilla or the mandible of the subject, independently as a first step, before the subsequent attachment of the arch bar to the bone fasteners. This allows for an easier and more accurate placement of the bone fasteners than the conventional approach of simultaneously attaching each arch bar fastener to the arch bar and the maxilla or mandible (e.g., by inserting the arch bar fastener through an attachment loop and screwing the fastener into the maxilla or mandible). By separating the two attaching functions (i.e., attaching the bone fasteners to the maxilla or mandible and attaching the bone fasteners to the arch bar), it is easier for a surgeon to position the bone fasteners as needed (e.g., between tooth roots) by not also requiring that the fastener be attached to the arch bar while it is being attached to the maxilla or mandible.

Figure 1:
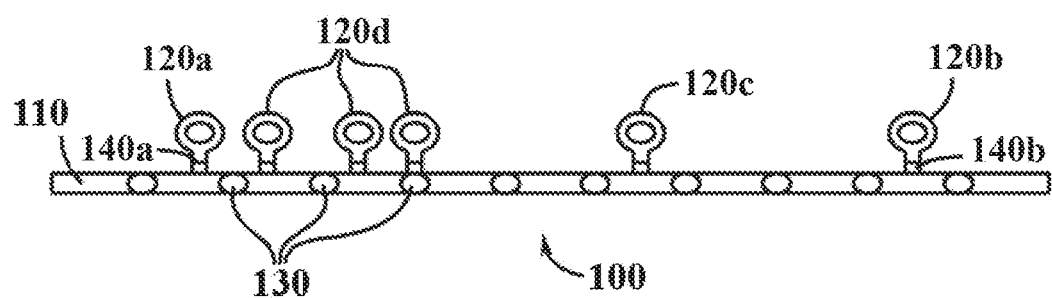
FIG. 1 is a frontal view of an arch bar prior to bending to approximate the shape of a mandible or a maxilla, according to one embodiment.
Figure 2:
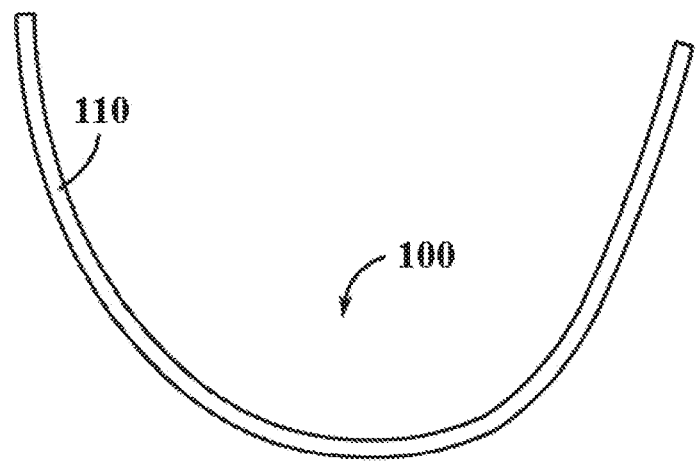
FIG. 2 is a top view of an arch bar bent into a shape to approximate a maxillary or mandibular arch, according to one embodiment.

As shown in FIG. 1, and according to one embodiment, an arch bar 100 is a bar 110 having a first attachment loop 120a, a second attachment loop 120b, and a plurality of hooks 130. The first attachment loop 120a is distally located to the second attachment loop 120b such that each end of the bar, may be secured to a bone such a mandible or maxilla, or a prosthedontic apparatus via the first and second attachment loops 120a, 120b. The attachment loops 120a, 120b may be attached to the bar 110 via a stem 140a or 140b that is rigid or bendable. In some embodiments, a portion of the stem 140 may be rigid or semi-rigid while the remainder of the stem 140 is flexible. The stem 140 may have a variety of cross-sectional shapes (e.g., rectangular, circular, oval, etc.). The bar 110 may be bendable to approximate a maxillary or mandibular arch, for example as shown in FIG. 2.

As used herein, the term "bendable" is to mean that the item to which the term refers may be moved, or shaped, in response to the application of an external force. Further, once moved or bent, the item does not return to its previous position, without being acted upon by a second external force. In other words, the item is bent and stays bent, until bent into another shape or position.

As used herein, the term "rigid" is used to refer to an item that resists bending to a moderate force, but may be bent under extreme force as compared to a bendable item.

The bar may be made from a variety of materials known to those of skill in the art. For example the bar may be made from stainless steel, titanium, or other metals; acrylics; and/or polymers.

In some embodiments, the bar 110 has one or more additional attachment loops 120c, 120d located between the first 120a and second 120b attachment loops. For example, the bar 110 may have a third attachment loop 120c located approximately midway between the first 120a and second 120b attachment loops, thereby providing an additional point of attachment for the bar.

The attachment loops 120 provide a point at which the bar 110 may be secured to a maxilla, a mandible, or a prosthetic appliance using a screw, a bone screw, or other fastener known to those of skill in the art. In some embodiment, the one or more additional attachment loops refers to a third, a fourth, a fifth, a sixth, a seventh, or more attachment loops that are even spaced along a length of the bar 110, or at other predetermined positions.

The attachment loops 120 may be integrally formed with the bar 110 as if a single piece of material were used and each portion cut or formed from the single piece. In other embodiments, the attachment loops 120 are made from a separate piece of material and attached to the bar 110 via welding, adhesive, rivets, screws, or via other attachments known to those of skill in the art. The material from which the attachment loops 120 may be made may be the same as the bar 110, or of a different material.

The attachment loops 120 may be appended from the arch bar 100 via a stem 140 that is bendable. A bendable stem provides for the individual adjustment of each attachment loop to a position that allows for insertion of a screw into bone and between the roots of adjacent teeth, or for other adjustment of the position as desired by the surgeon or other medical professional.

A variety of fasteners may be used to attach the bar 110 to a maxilla or a mandible. For example, such fasteners may include screws, rivets, bolts, staples, or other fastener known to those of skill in the art. The fasteners are attached to the maxilla or mandible via a variety of systems. For example, a hole for attaching the fastener may be pre-drilled in the maxilla or mandible, or the fastener may be a self-drilling or self-tapping fastener. The size of the fastener may also be varied depending upon the placement desired. For example, mandibles are typically thicker than maxillas and therefore a mandible is capable of receiving a longer and/or wider fastener than the maxilla. Fasteners may also be flush mounted to the gingiva or may have a relief from the gingival surface so that there is some amount of externalization for a surgeon or dental professional to easily find the fastener when removal of the device is desired.

Figure 3:
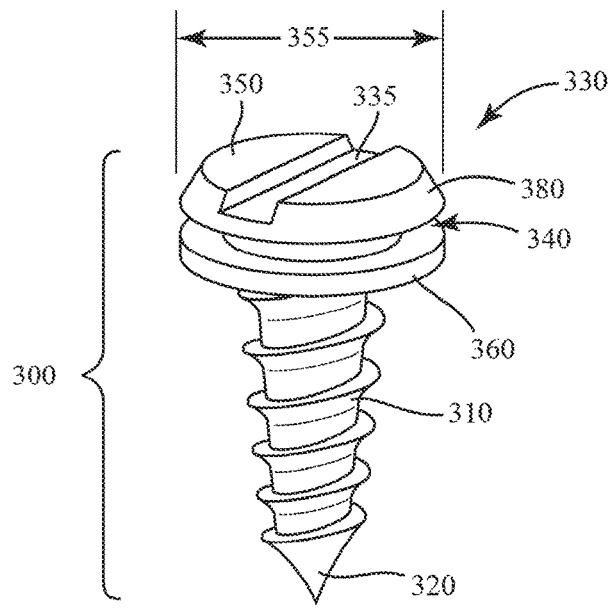
FIG. 3 is a perspective view of an arch bar fastener, according to one embodiment.

FIG. 3 shows a bone fastener 300 according to an exemplary embodiment. The bone fastener 300 is shown as a bone screw having a threaded shaft 310, a tip 320, and a head 330. The bone screw may be inserted into a bone such as a maxilla or mandible via a pilot hole that was previously drilled, or the tip and shaft may be configured to be self-drilling or self-tapping.

The head 330 of the bone fastener 300 may have a slotted drive mechanism 335 for engaging a slotted screwdriver to drive the bone fastener 300 into bone. The slotted drive mechanism 335 is shown only as an example, as alternatively the drive mechanism may be able to be engaged by a Phillips driver, a star driver, an Allen wrench, or other driver, wrench, or tool known to those of skill in the art. Alternatively, the head 330 may be shaped as a hex-head or any shape known to those of skill in the art for engaging a driver for the screw.

The head 330 includes a circumferential groove 340 (e.g., indentation, recess, slot, etc.) configured to receive one of the attachment loops 120. The groove 340 is formed by a support 342 that separates an upper portion 350 of the head 330 from a lower portion 360. The upper portion 350 and the lower portion 360 each have a width 355 that is greater than the minimum dimension 365 (e.g., diameter) of the openings 370 in the attachment loops 120. In another embodiment, the arch bar 110 may be coupled to one or more bone fasteners 300 by an elongated slot formed in the arch bar 110, where the minimum dimension (e.g., width) of the slot is less than the width 355.

The screw may project through the gingiva or mucosa for ease in removal, or it may be designed to sit flush with the bone. To secure the arch bar to the maxilla or the mandible, insertion of the bone fasteners 300 into a root should be avoided. In fact, it is desired that the bone fasteners 300 are inserted into the bone at positions between the roots of adjacent teeth. After the bone fasteners 300 have been inserted into the bone, the attachment loops 120 of the arch bar 100 is coupled to the bone fasteners 300.

Figures 4A, 4B:
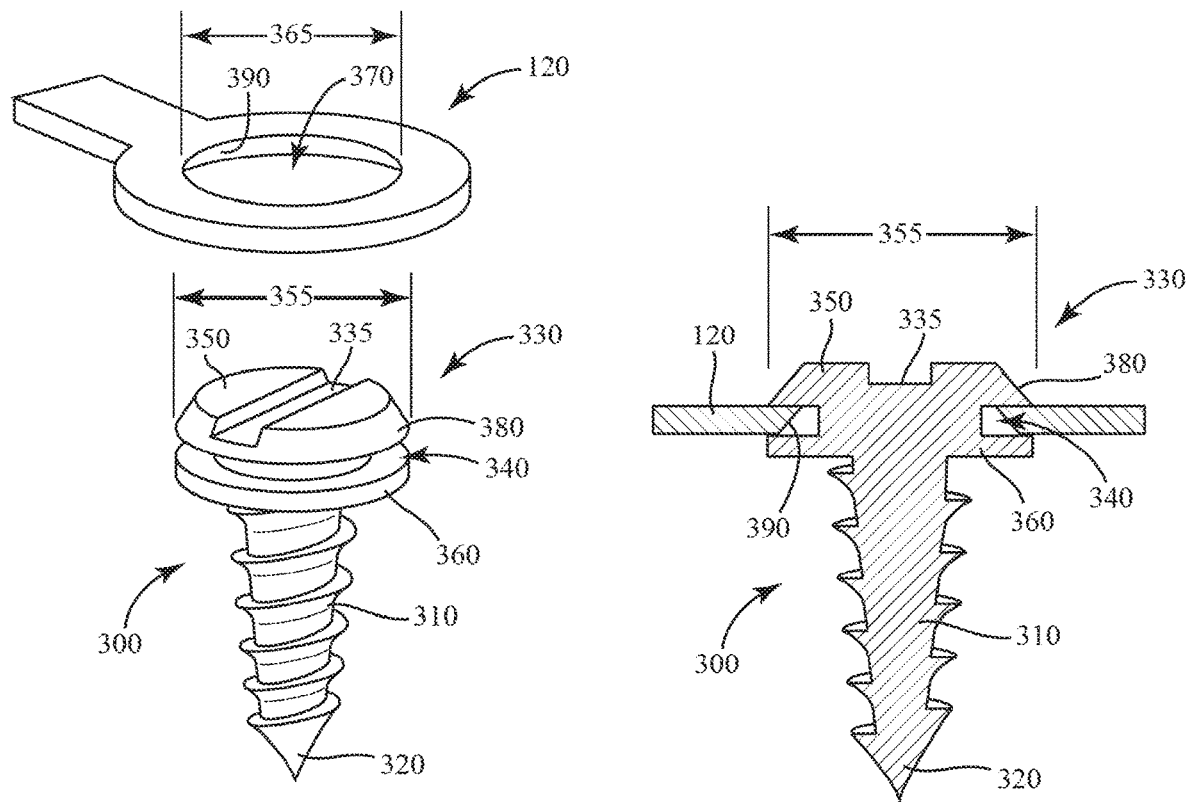
FIG. 4A is a perspective view of the arch bar fastener of FIG. 3 and an attachment loop of an arch bar, according to one embodiment.
FIG. 4B is a cross-section view of the arch bar fastener of FIG. 3 coupled to and an attachment loop of an arch bar, according to one embodiment.

FIGS. 4A-4B show the attachment loop 120 coupled to the bone fastener 300. According to an exemplary embodiment, the upper portion 350 may include a beveled edge 380. The bottom face of the attachment loop 120 may include a beveled edge 390 surrounding the opening 370. The attachment loop 120 is pressed onto the bone fastener 300 and the upper portion 350 is forced through the opening 370. The attachment loop 120 is therefore trapped in the groove 340, between the upper portion 350 and the lower portion 260 of the head 330 to attach or secure the attachment loop 120 to the fastener. The beveled edges 380 and 390 provided ramped surfaces to facilitate the insertion of the upper portion 350 through the opening 370, coupling the attachment loop 120 to the bone fastener 300 without the use of an additional fastening device.

In some embodiments, the attachment loop 120 and/or the bone fastener 300 may be formed from an alloy or other material with a modulus of elasticity that allows sufficient deformation between the components to allow the upper portion 350 to pass through the opening 370 without the application of an excessive force (e.g., one that would injure or cause excessive discomfort to the subject). That is, the attachment loop 120 and/or the bone fastener 300 deform so that a person may attach or secure the arch bar 100 to the bone fasteners 300 by "snapping" the attachment loop 120 onto the bone fasteners 300 by hand.

The shape of the head 330 as shown in FIGS. 3-4B is exemplary only. In other embodiments, the head 330 may be otherwise shaped to have an upper portion with a first width that is greater than the opening 370 in the loop 120 and portion with a lesser width configured to receive the loop 120. As shown in FIGS. 3-4B, the head 330 may be a relatively low profile head. In other embodiments, the head 330 may have a higher profile with a more conical shape. In other embodiments, the head 330 may be otherwise shaped. For example, as shown in FIG. 5, the head 330 may be formed with a round upper portion 550 and a groove 540 separating the round upper portion 550 from a lower portion 560.

In other embodiments, the loop 120 may be otherwise coupled to the head of the bone fastener 300. As shown in FIG. 6, a loop 620 may be an open loop that is configured to be received by the groove 340 of the head 330 of a bone fastener 300 from the side rather than over the top of the head 330. A slot 673 extends through the loop 620 to the aperture 670, dividing the loop 620 into two portions, 675 and 677. The two portions 675 and 677 are movable relative to one another by a limited amount that is at least sufficient to allow the head 330 of the bone fastener 300 to pass though the slot 673 to the aperture 670. As illustrated, the support 342 of the head 330 is wider than the slot 673 and passing the support 342 through the slot 673 cause the two portions 675 and 677 of the loop 620 to move relative to one another to all allow the support 342 to move into the aperture 670, thereby positioning the loop 620 within the groove 340 to attach or secure the loop 620 to the bone fastener 300. Additionally, the portions 675 and 677 may be crimped, wrapped about one another, or otherwise secured to one another to help secure the loop 620 to the bone fastener 300.

In still other embodiments, the arch bar 100 may be otherwise coupled to the bone fastener 300. For example, as shown in FIGS. 7-11, arch bar 100 may not include loops but may instead be coupled to the bone fasteners 300 with flexible elongated stems 740 (e.g., tabs, bars, protrusions, etc.) that are bent or wrapped about a portion of the bone fastener 300. Bending or wrapping the stem 740 about a portion of the bone fastener 300 includes situations where the stem 740 is bent or wrapped about the fastener for less than one revolution, for one revolution, and for more than one full revolution. The stems 740 are configured to be relatively flexible to facilitate being bent or wrapped about the bone fastener 300. The stems 740 may, for example be formed from a relatively flexible alloy, or may be treated (e.g., annealed) to increase flexibility. The stems 740 may be solid with various cross sectional shapes (e.g., rectangular, circular, oval, etc.) or may be formed from several smaller stands (e.g., braided or twisted strands).

Figure 8:
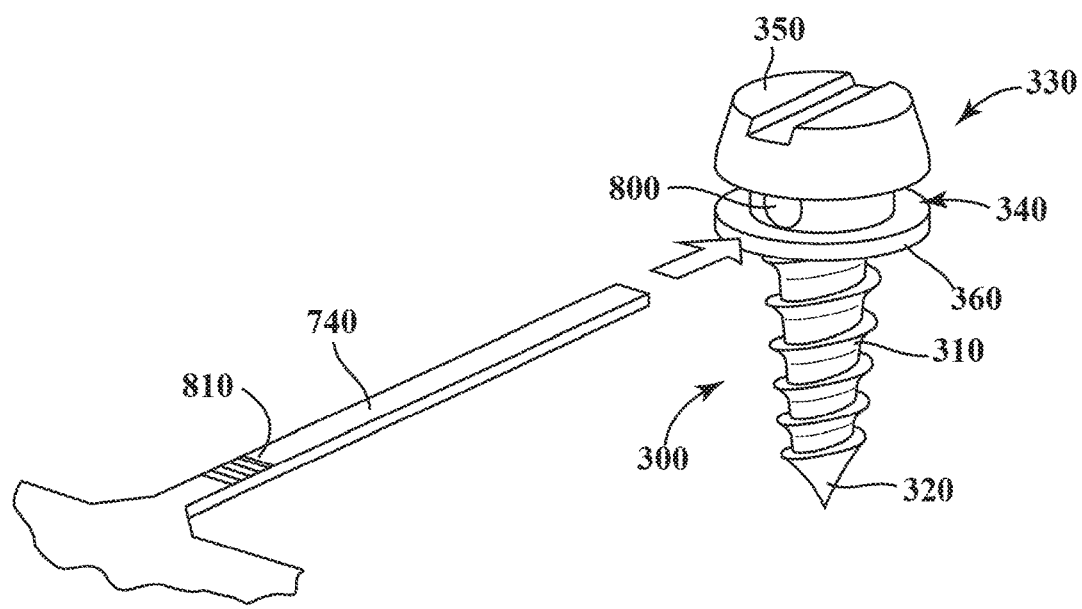
FIG. 8 is a perspective view of an arch bar fastener and an elongated stem of an arch bar, according to one embodiment.

As shown in FIG. 8, in one embodiment, the stem 740 is inserted into a through hole 800 formed in the support 342 of the head 330 of the bone fastener 300. The stem 740 may then be wrapped about the head 330 of the bone fastener 300. The stem 740 and/or the head 330 may be contoured or textured to inhibit the relative motion between the stem 740 and the bone fastener 300 in one or more directions. For example, the stem 740 and/or the head 330 may be formed with a ratchet mechanism allowing the stem 740 to be inserted into the hole 800 but inhibiting the removal of the stem 740 from the hole 800. A set mark 810 may be provided on the surface of the stem 740 to indicate the amount of the stem 740 to be inserted into the hole 800 to achieve a preferred position of the arch bar 110 relative to the bone fastener 300. In some embodiments, the stem 740 may include multiple set marks. A stop 745 may be provided to limit the insertion of the stem 740 into the hole 800.

Figure 9:
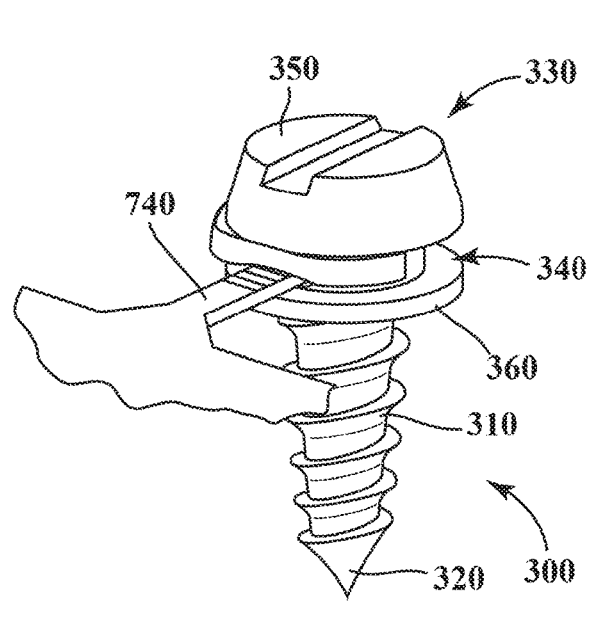
FIG. 9 is a perspective view of an arch bar fastener coupled to an elongated stem of an arch bar, according to one embodiment.
Figure 10:
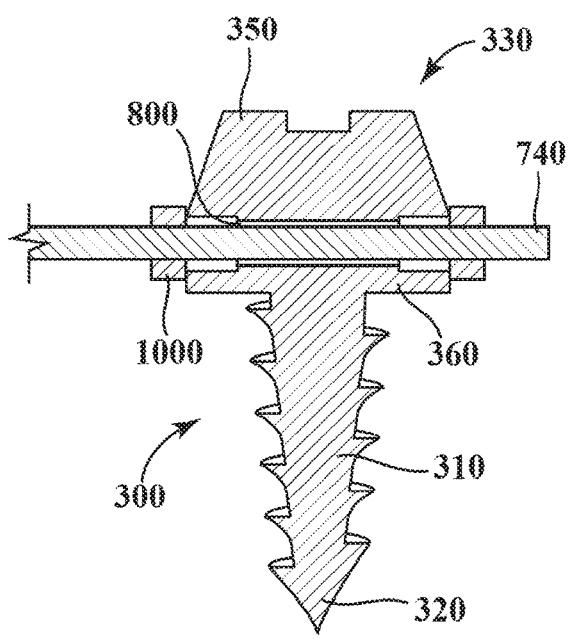
FIG. 10 is a cross-section view of an arch bar fastener coupled to an elongated stem of an arch bar, according to another embodiment.

The stem 740 may be wrapped around the head 330, as shown in FIG. 9 (e.g., about the support 342 and within the groove 340). In other embodiments, the stem 740 may be wrapped vertically around the head 330 (e.g., around the upper portion 350), or any other direction around the head 330 to prevent the stem 740 from being withdrawn back through the hole 800. The stem 740 may be otherwise fixed in relation to the bone fastener 300 after passing through the hole 750. For example, a stopper 1000 may be coupled to the stem 740 on either side of the hole 800 to prevent the stem 740 from being withdrawn back through the hole 800, as shown schematically in FIG. 10. The stopper 1000 may be a separately applied fixation clip. In another embodiment, the stem 740 may be crimped or otherwise deformed on either side of the hole 800 to prevent the stem 740 from being withdrawn back through the hole 800.

In other embodiments, the stem 740 may not pass through a through hole in the head 330 but may instead simply be wrapped around the head 330 (e.g., wrapped around the groove 340). The head may include outwardly extending features (e.g., arms) around which the stem 740 may be wrapped.

Referring now to FIG. 11, in some embodiments, the stem 740 may have varied physical properties along its length. For example, The stem 740 may include a first portion 1100 proximal to the bar 110 that is relatively stiff or semi-rigid and a second portion 1110 distal to the bar 110 that is relatively flexible. In one embodiment, the first portion 1100 has a width that is greater than the width of the second portion 1110. The set mark 810 may, in some embodiments, be disposed at the border between the first portion 1100 and the second portion 1110.

In some embodiments, the base of the head of the bone fastener 300 (e.g., the lower portion 360) is of a larger diameter than a shaft of the bone fastener 300 to permit solid coaptation (via surface area contact) of the arch bar to the bone, much like a washer. Wire or elastics may then be placed between the arch bar opposing hooks 130, or tabs, therefore a passage hole through the screw is not required, as was common with IMF screw fixation.

As noted above, a plurality of hooks 130 are attached to the bar 110. As used herein, plurality may mean one, but typically means more than one, such as two, three, four, five, six, seven, eight, nine, ten, eleven, twelve, thirteen, fourteen, fifteen, sixteen, seventeen, eighteen, nineteen, or twenty. The hooks 130 are used to attach a wire, an elastic such as a rubber band, or other device known to those of skill in the art, to the bar 110 to immobilize, stabilize, or fixate the maxilla to the mandible, thus allowing for healing of the respective bones.

As depicted in FIG. 12, the hooks 130 may have the open part of the hook in a position opposed to the attachment loop. However, in other embodiments, the hook may have the open part of the hook turned toward the attachment loop. In such other embodiments, the attachment loops and hooks may be staggered in position so that the hook does not interfere with attaching the attachment loop to the bone fastener. The size, shape, and configuration of the hooks may vary according to design preferences. The common mandatory design element is the ability to satisfactorily allow placement of wire, elastic, or other fasteners.

In some aspects, the medical apparatus has two arch bars, as shown in FIG. 13. A first arch bar 1300 is attached to the maxilla and a second arch bar 1400 is attached to a mandible. The bars 1310, 1410 are attached to bone fasteners 300 that have previously been attached to the maxilla and mandible. The hooks 1330, 1430 on each of the arch bars 1300, 1400 opposed to one another so that the securing wires 1380, elastics such as rubber bands, or other attachment devices can be hooked to the arch bars 1300, 1400 on the maxilla and mandible. The securing wires 1380 or other attachment devices may be separate entities as shown in FIG. 13, or a single wire may be intricately woven to attach arch bar 1300 to arch bar 1400, thus fixating the maxilla and/or mandible.

Figure 14:
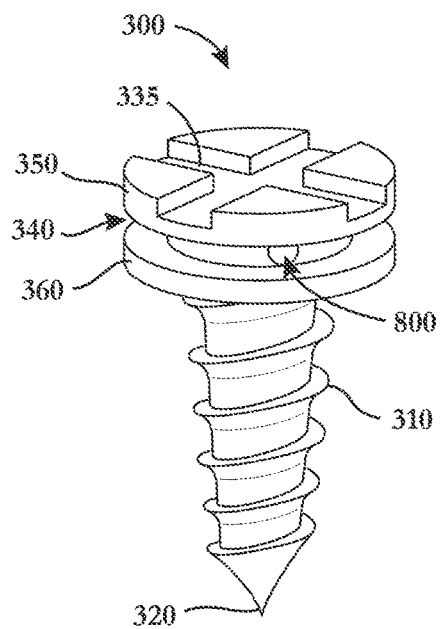
FIG. 14 is a perspective view of a screw, according to one embodiment.
Figure 15:
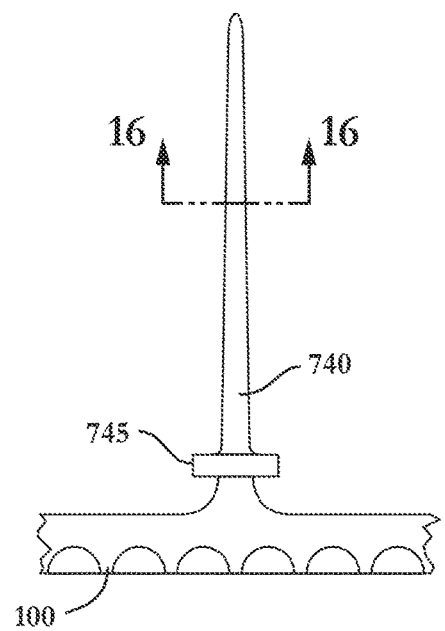
FIG. 15 is a side view of a portion of an arch bar, according to one embodiment.
Figure 16A:
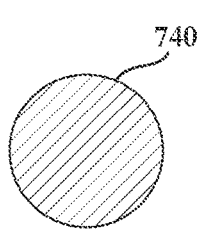
FIGS. 16A-16C are sectional views along line 16 of the arch bar of FIG. 15, according to exemplary embodiments.
Figure 16B:
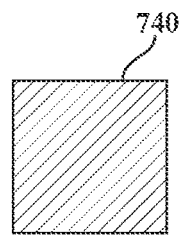
Figure 16C:
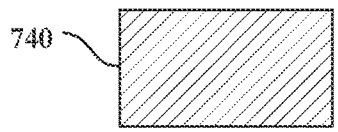
Figure 17:
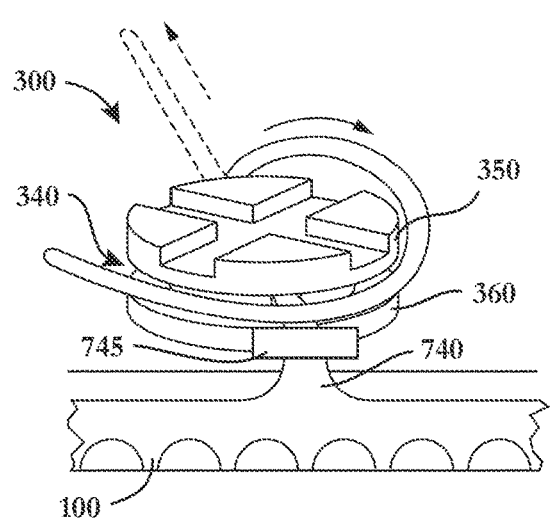
FIG. 17 is a perspective view of the screw of FIG. 14 and the arch bar of FIG. 15.

Referring to FIG. 14, a bone fastener 300 is illustrated according to an exemplary embodiment. The bone faster 300 includes a Phillips-head drive mechanism 335. Referring to FIG. 15, a portion of an arch bar 100 is illustrated according to an exemplary embodiment. The stem 740 includes a stop located near the bar 100 to limit insertion of the stem 740 into the hole 800 of the screw 300. FIGS. 16A, 16B, and 16C show exemplary cross sections of the stem 740. In some embodiments, the shape of the hole 800 of the screw 300 matches the particular cross section of the stem 740. Referring to FIG. 17, an exemplary method of securing the screw 300 to the bar 100 via the stem 740 is illustrated. As shown by the arrows, the stem 740 is first inserted through the hole 800 of the screw 300 and then wrapped around the screw 300 in the groove 340.

Figure 18:
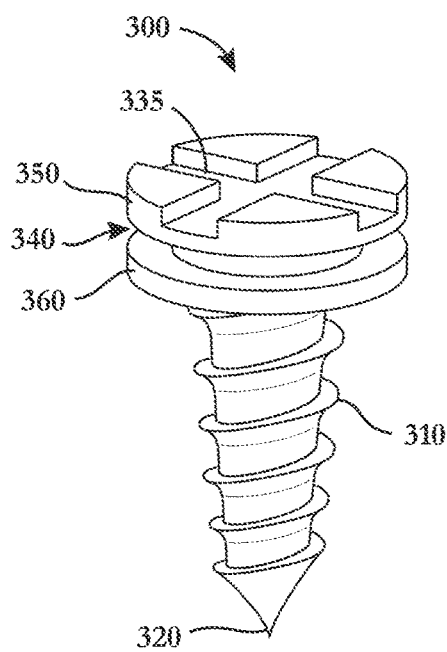
FIG. 18 is a perspective view of a screw, according to one embodiment.
Figure 19:
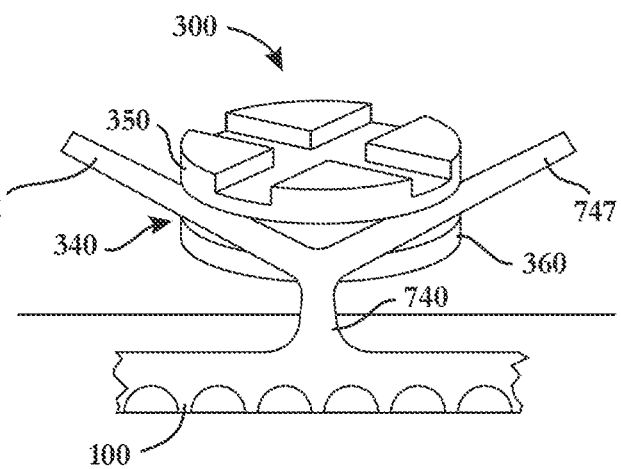
FIG. 19 is a side view of a portion of an arch bar, according to one embodiment.
Figure 20:
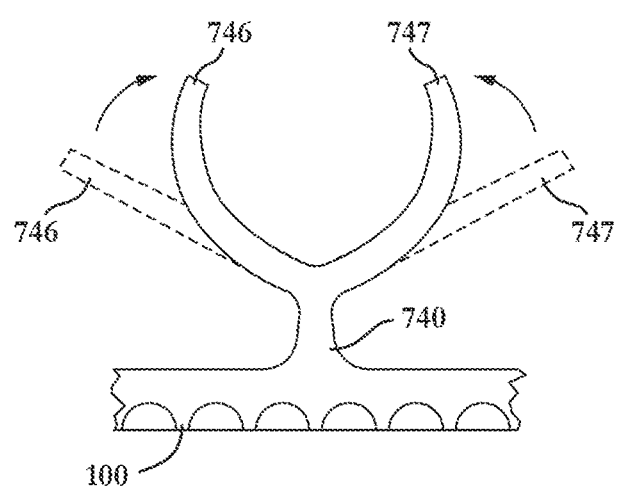
FIG. 20 is a perspective view of the screw of FIG. 18 and the arch bar of FIG. 19.
Figure 21:
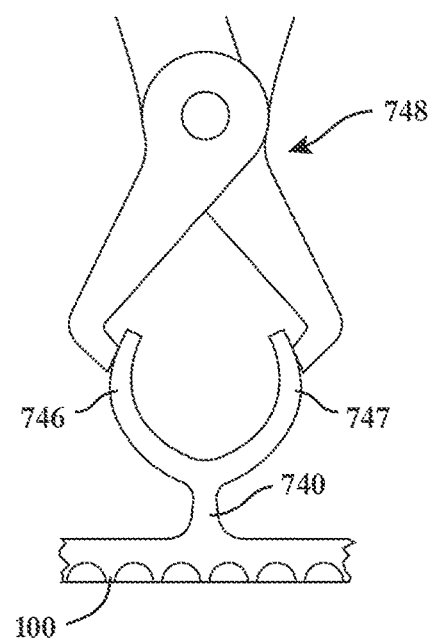
FIG. 21 is a side view of a portion of an arch bar, according to one embodiment.

Referring to FIG. 18, a bone fastener 300 is illustrated according to an exemplary embodiment. The illustrated bone fastener 300 is similar to the bone fastener illustrated in FIG. 14, except that it does not include a hole 800 and instead only includes the groove 340 for securing the bone fastener to a stem of an arch bar. Referring to FIG. 20, an alternative stem 740 having an open-loop arrangement including two arms 746 and 747 is illustrated according to an exemplary embodiment. The two arms 746 and 747 extend in opposite directions from a central location. The arms 746 and 747 are flexible. Referring to FIG. 19, an exemplary method of securing the screw 300 to the bar 100 via the stem 740 is illustrated. As shown by the arrows, each arm 746 and 747 is wrapped around the screw 300 in the groove 340, with the arms 746 and 747 being wrapped around the screw 300 in opposite directions (e.g., clockwise and counterclockwise). Referring to FIG. 21, a pliers 748 or other crimping tool may be used to secure the stem 740 having the two arms 746 and 747.

Figure 22:
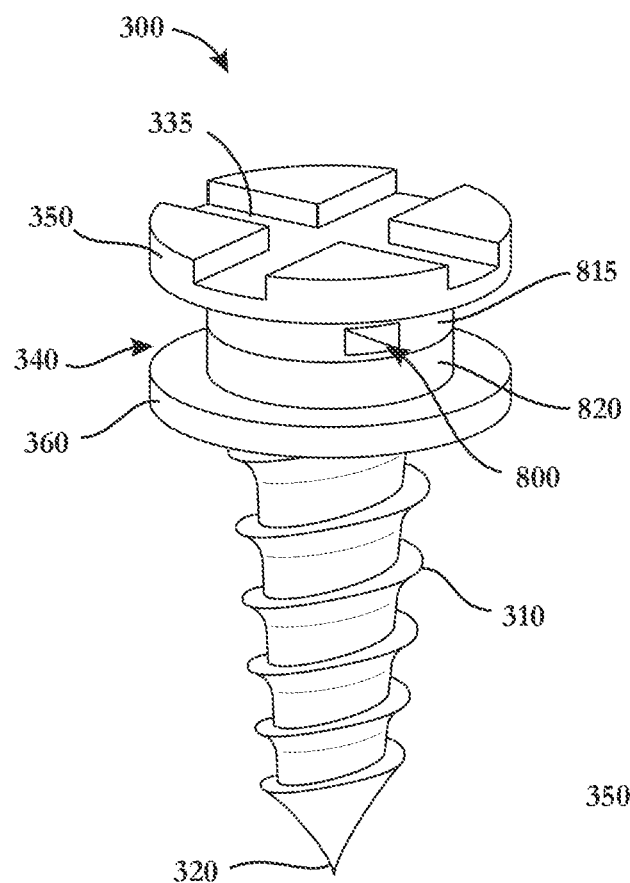
FIG. 22 is a perspective view of a screw, according to one embodiment.
Figure 23:
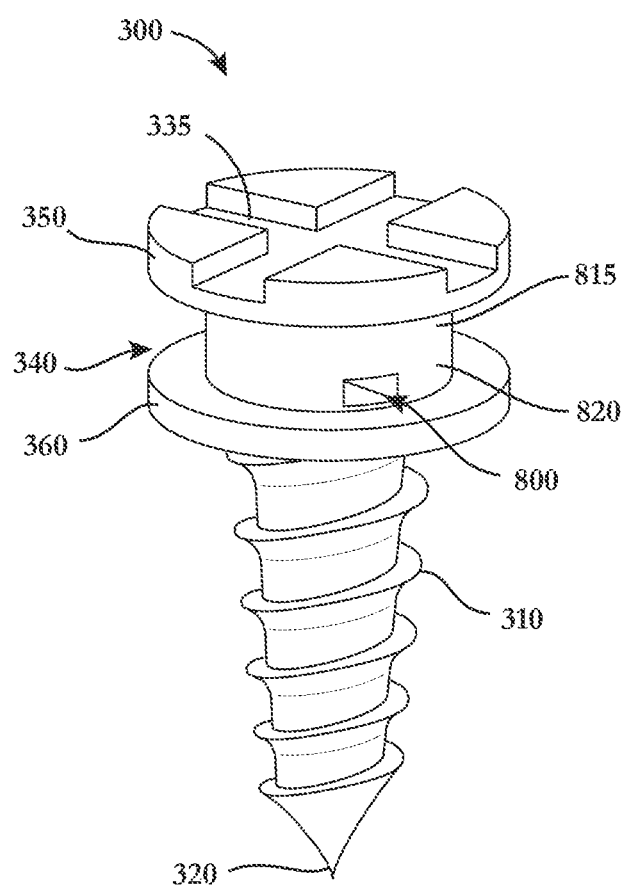
FIG. 23 is a perspective view of a screw, according to one embodiment.

Referring to FIG. 22, a bone fastener 300 is illustrated according to an exemplary embodiment. The illustrated bone fastener 300 is similar to the bone fastener illustrated in FIG. 14, except that the groove 340 is taller and includes a top portion 815 that includes the hole 800 and a bottom portion 820 that does not include the hole. The taller groove 340 provides increased surface area for wrapping the stem 740 around the screw 300, which may help to better secure the screw 300 to the arch bar 100. Referring to FIG. 23, a bone fastener 300 is illustrated according to an exemplary embodiment. The illustrated bone fastener 300 is similar to the bone fastener illustrated in FIG. 23, except that the hole 800 is located in the bottom portion 820 of the groove, not the top portion 815. Referring to FIG. 24, an exemplary method of securing the screw 300 to the bar 100 via the stem 740 is illustrated. As shown by the arrow in FIG. 25, the stem 740 is first inserted through the hole 800 of the screw 300 and then wrapped around the screw 300 in the upper portion 815 of the groove 340. FIGS. 22-25 illustrate a screw 300 including a pass-through channel 800 (i.e. through-hole variation) with sufficient space beneath the hold to bend the stems 740 (i.e. elongated extensions from the arch bar such as tabs, wires, flanges, etc.) around, above, or below the pass-through channel 800. The stems 740 are located close to one another to allow for selection of the appropriate stem 740 for attachment to the previously placed screw 300. In some embodiments, the stems 740 have a wire-sized gauge (e.g. 15-20 gauge). In some embodiments, there is sufficient room in the gap 340 of the screw 300 to accommodate one or more wraps of the stem 740 around the screw 300. In other embodiments, there is sufficient room in the gap 340 of the screw 300 to accommodate two or more wraps of the stem 740 around the screw 700. In yet other embodiments, the stem 740 may be wrapped, or passed back under itself.

Figure 27:
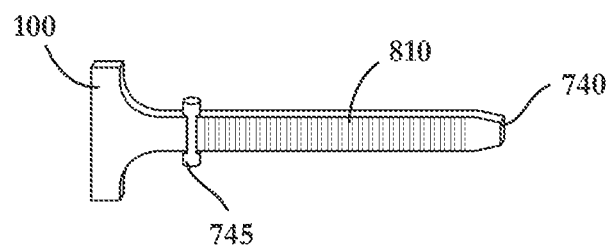
FIG. 27 is a side view of a portion of the arch bar of FIG. 26.
Figure 28:
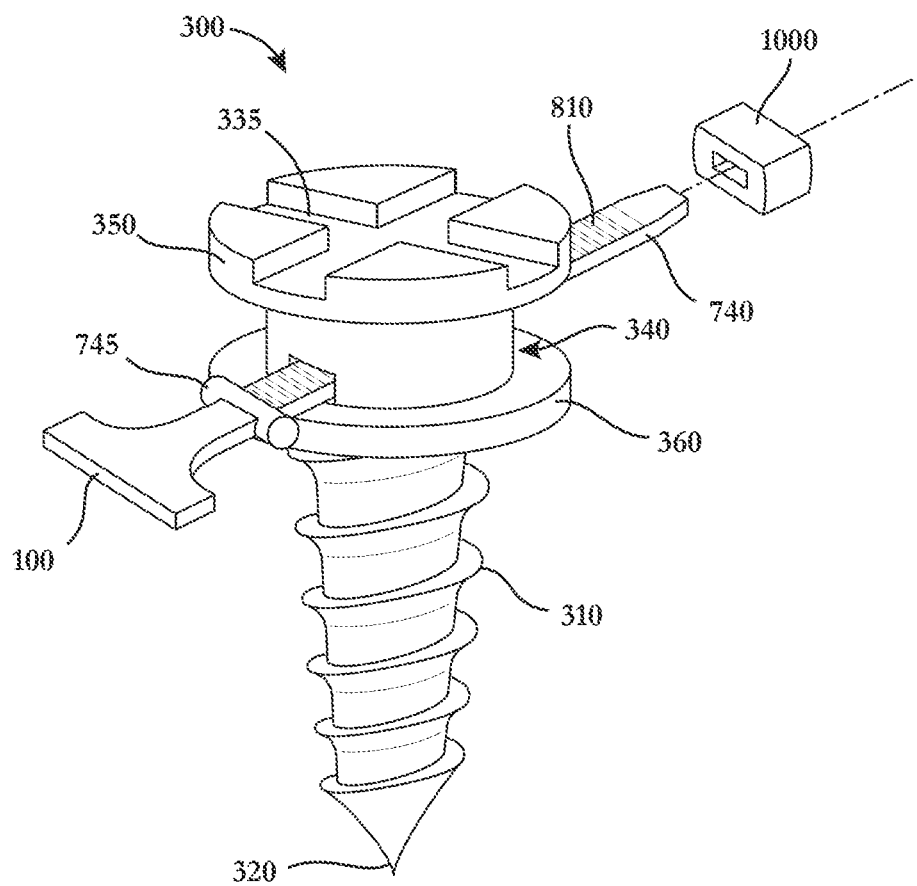
FIG. 28 is a perspective view of a screw and the arch bar of FIG. 26.

Referring to FIG. 26, an arch bar 100 is illustrated according to an exemplary embodiment. The stems 740 include a number of ridges and grooves 810 (e.g., serrations) that interact with a stopper or fastener 1000 (FIG. 28) to secure the screw 300 to the arch bar 100. The ridges and grooves 810 and the stopper 1000 may interact in the manner of a zip-tie that allow the stopper 1000 to be slid onto the stem 740 in a first direction and prevent removal of the stopper 1000 from the stem 740 in an opposite direction. FIG. 27 illustrates an exemplary embodiment of a stem 740 including a stop 745 for limiting inserting of the stem 740 into a hole 800 of a screw 300. In some embodiments, the length the stem 740 extends from the bar 100 is no more than 3 centimeters. Referring to FIG. 28, an exemplary method of securing the screw 300 to the bar 100 via the stem 740 is illustrated. As shown by the arrow, the stopper 1000 is slid onto the stem 740 to secure the stem 740 to the screw 300 after the stem has been inserted into the hole 800 of the screw 300. The stem 740 has a stop 745 on an arch bar 100 inserted into the pass-through channel 800 of a screw 300, according to one embodiment, where the serrations 810 may then be engaged by a locking feature 1000 that slides over the stems 740 and engages the serrations 810, or the serrations 810 may be engaged within a head of the screw 300 without the use of the locking feature 1000. In one embodiment, the screws 300 are placed in to the mandible or maxilla of a subject, the stems or tabs 740 of the arch bar 100 are then aligned with the pass-through channels 800 of the screws 300 and inserted therein. The positioning of the arch bar 100 is then adjusted if needed. Where the serrations 810 on the stems 470 are not engaged by counter serrations in the head of the screw 300, the locking feature 1000 is then slid over the stem 740 and the excess stem length is cut off.

In another aspect, methods are provided for stabilizing a mandibular arch or a maxillary arch using the medical apparatuses described above. For example, the arch bar may be bent to approximate the mandibular arch or the maxillary arch of a patient in need of stabilization or fixation of the mandibular and/or maxillary arch. Screws or bone fasteners are attached or secured in the mandible and/or maxilla and the arch bar is then attached to the screws.

In other embodiments, where both a mandibular and a maxillary arch bar are used, the methods also include securing a wire, an elastic, or other flexible or semi-rigid material between the hooks of the mandibular arch bar and the hooks of the maxillary arch bar. This may be done to establish intermaxillary fixation or dental occlusion. Such methods are known as wiring the jaws shut or intermaxillary fixation. The securing device used to fasten or secure the two arch bars to one another may also further secure each arch bar to the bone fasteners as the tension in the securing device pulls the two arch bars toward one another and against the bone fasteners.

The above described apparatuses and methods are used to restore, fixate, or create a new dental occlusion between existing native dentition, dental implants, or other dental appliances, or for the treatment of fracture and/or reconstructing maxillary and/or mandibular reconstruction.

The embodiments illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Additionally the phrase "consisting essentially of" will be understood to include those elements specifically recited and those additional elements that do not materially affect the basic and novel characteristics of the claimed invention. The phrase "consisting of" excludes any element not specifically specified.

One skilled in the art will readily realize that all ranges discussed can and do necessarily also describe all subranges therein for all purposes and that all such subranges also form part and parcel of this invention. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, it should be understood that changes and modifications can be made therein in accordance with ordinary skill in the art without departing from the invention in its broader aspects as defined in the following claims.

What is claimed is:

1. A medical apparatus comprising:
 a plurality of bone fasteners configured for attachment to a mandible, a maxilla, a bone graft, or a prosthodontic jaw portion of a subject, each bone fastener comprising:
  a head having an upper portion separated from a lower portion by a groove, and
  a shaft extending from the lower portion;
 a prosthodontic appliance configured for attachment to the bone fasteners, the prosthodontic appliance comprising:
  a plurality of attachment loops, each attachment loop defining an aperture for receiving one of the bone fasteners, a bottom face of each attachment loop comprising a beveled edge surrounding the aperture;
 wherein the aperture of each attachment loop is configured to allow the upper portion of the head of one of the bone fasteners to pass therethrough so that the aperture is positioned within the groove to secure the prosthodontic device to the bone fastener, the beveled edge providing a ramped surface to facilitate the insertion of the head through the aperture without the use of an additional fastening device.

2. The medical apparatus of claim 1, wherein the upper portion of the head of each bone fastener is contoured to allow the upper portion to pass through the aperture of one of the attachment loops.

3. The medical apparatus of claim 2, wherein the contour comprises a beveled edge to allow the upper portion to pass through the aperture of one of the attachment loops.

4. The medical apparatus of claim 1, wherein the upper portion of the head of each bone fastener is rounded to allow the upper portion to pass through the aperture of one of the attachment loops.

5. The medical apparatus of claim 1, wherein the head of each bone fastener further includes a drive mechanism for engagement by a tool for driving the bone fastener; and wherein the shaft of each bone fastener is threaded.

6. The medical apparatus of claim 1, wherein the aperture has a minimum dimension, wherein a minimum dimension of the upper portion of each bone fastener is greater than the minimum dimension of the aperture, and wherein a minimum dimension of the lower portion of each bone fastener is greater than the minimum dimension of the aperture.

7. A medical apparatus comprising:
 a plurality of bone fasteners configured for attachment to a mandible, a maxilla, a bone graft, or a prosthodontic jaw portion of a subject, each bone fastener comprising:
  a head having an upper portion separated from a lower portion by a groove, and
  a shaft extending from the lower portion;
 a prosthodontic appliance comprising:
  a plurality of attachment tabs, each attachment tab including a first portion and a second portion divided by a slot, wherein each attachment tab forms an open loop that is disconnected at the slot, and wherein the first portion and the second portion define an aperture therebetween and are configured for limited movement relative to one another;
 wherein each attachment tab is configured to allow the head of one of the bone fasteners to pass through the slot and into the aperture so that the first portion and the second portion are positioned within the groove of the head to secure the attachment tab to the one of the bone fasteners.

8. The medical apparatus of claim 7, wherein the head of each bone fastener further includes a drive mechanism for engagement by a tool for driving the bone fastener; and wherein the shaft of each bone fastener is threaded.

* * * * *